United States Patent
Abu-Tarif et al.

(10) Patent No.: US 11,684,461 B2
(45) Date of Patent: Jun. 27, 2023

(54) INTRAORAL SCANNING SYSTEM USING LIGHT PATTERNS BASED ON PATH TRAVERSAL

(71) Applicant: MEDIT CORP., Seoul (KR)

(72) Inventors: Asad Abu-Tarif, Irvine, CA (US); Saradwata Sarkar, Redondo Beach, CA (US)

(73) Assignee: MEDIT CORP., Seoul (KR)

( * ) Notice: Subject to any disclaimer, the term of this patent is extended or adjusted under 35 U.S.C. 154(b) by 376 days.

(21) Appl. No.: 17/130,343

(22) Filed: Dec. 22, 2020

(65) Prior Publication Data

US 2021/0186667 A1   Jun. 24, 2021

Related U.S. Application Data

(60) Provisional application No. 62/952,837, filed on Dec. 23, 2019.

(51) Int. Cl.
  *A61C 9/00*   (2006.01)
  *A61B 1/24*   (2006.01)

(52) U.S. Cl.
  CPC .............. *A61C 9/006* (2013.01); *A61B 1/24* (2013.01); *G06T 2210/41* (2013.01)

(58) Field of Classification Search
  CPC ......... A61C 9/006; A61C 9/0053; A61B 1/24; A61B 1/00096; A61B 1/00172; A61B 1/0019; G06T 2210/41; G06T 17/00
  See application file for complete search history.

(56) References Cited

U.S. PATENT DOCUMENTS

| | | | | |
|---|---|---|---|---|
| 9,439,568 | B2 * | 9/2016 | Atiya | A61B 1/000094 |
| 11,583,166 | B2 * | 2/2023 | Tanaka | A61B 1/00194 |
| 2010/0284589 | A1 * | 11/2010 | Thiel | A61C 9/006 348/66 |
| 2016/0000535 | A1 * | 1/2016 | Atiya | A61B 1/00011 433/29 |
| 2018/0235738 | A1 * | 8/2018 | Atiya | G01B 11/24 |
| 2019/0388194 | A1 * | 12/2019 | Atiya | G01B 11/2513 |
| 2021/0140763 | A1 * | 5/2021 | Pesach | G06T 7/586 |
| 2021/0212806 | A1 * | 7/2021 | Sorimoto | A61B 1/00006 |

* cited by examiner

*Primary Examiner* — Roy M Punnoose
(74) *Attorney, Agent, or Firm* — Sughrue Mion, PLLC

(57) ABSTRACT

A scanning system is described herein which incorporates projecting a plurality of patterns onto an object of interest and capturing the reflected image. Each pattern is based at least in part on traversing a hypercube graph or a Fibonacci cube graph using a Hamiltonian path. The patterns are used to help define the three-dimensional shape of the underlying object of interest, while also providing more robust error-correcting properties. After the reflected image of the projected pattern is captured, the scanning system further processes and displays a three-dimensional model of the captured object of interest.

20 Claims, 7 Drawing Sheets

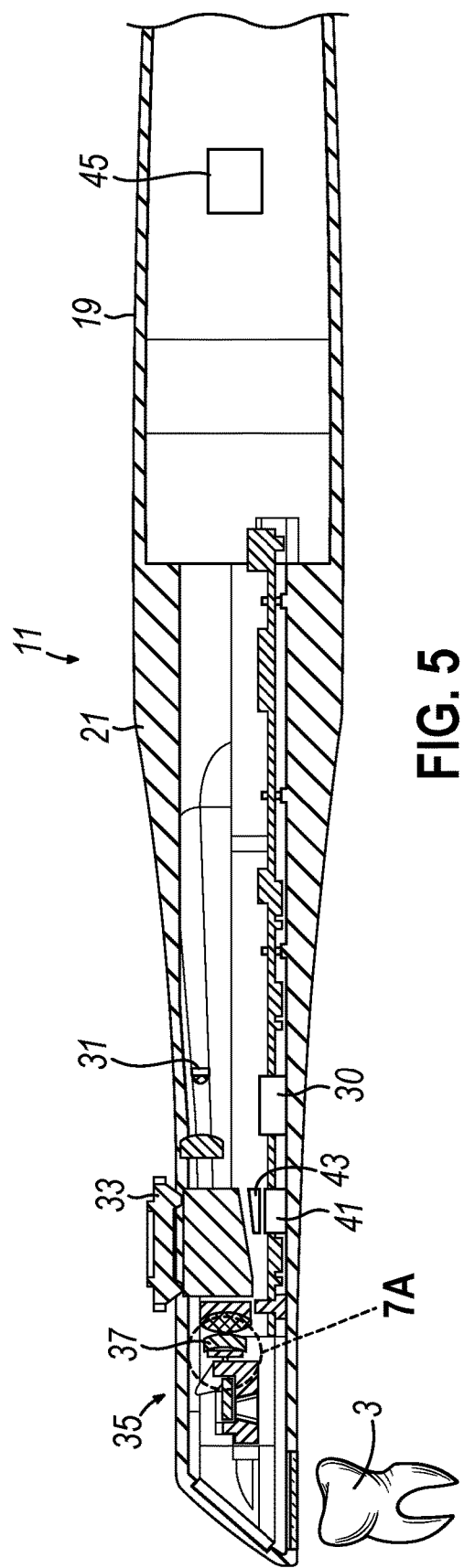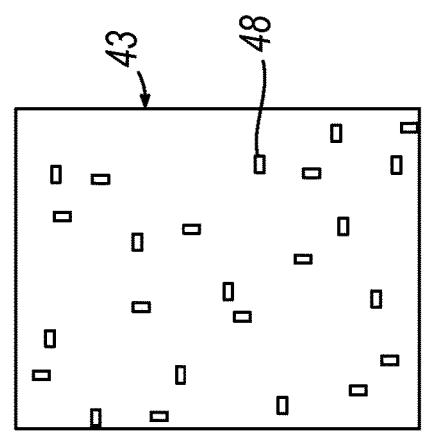

INTRAORAL SCANNING SYSTEM USING LIGHT PATTERNS BASED ON PATH TRAVERSAL

BACKGROUND

In the dentistry context, intraoral scanning may be used to capture images of a patient's teeth and gingival structure. These images may then be used to create and project a digital three-dimensional image of the teeth and gingival structure to a dentist or oral surgeon for use and manipulation in treating the patient. However, with respect to scanning, teeth are poorly reflective and possibly include stains or other inconsistencies regarding surface reflectiveness. Further, a patient's mouth can only provide limited space for which to illuminate and scan the structures therein. Thus, light beams reflected off teeth can only provide a limited understanding of the three-dimensional features of the teeth.

Projecting a grid or horizontal pattern on to teeth allows the pattern to deform when striking surfaces. This deformation allows vision/sensor systems to calculate the three-dimensional depth and surface information of object of interest. However, errors often occur in the digital modeling due to surface inconsistencies and these errors are difficult to determine and correct, particularly during the scanning process while the patient is in the office having their teeth scanned. It is understandably inconvenient for both doctor and patient to schedule and re-perform a digital scanning session if errors in the imaging occur. Thus, a need exists in the intraoral scanning field for more robust error realization and correction in essentially real-time in furtherance of a more efficient scanning procedure.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 5 depicts a cross-sectional view taken along line 5-5 of FIG. 3;

FIG. 6 depicts a top plan view of an exemplary coded mask for use by the sensor module of FIG. 4;

Figure 1:
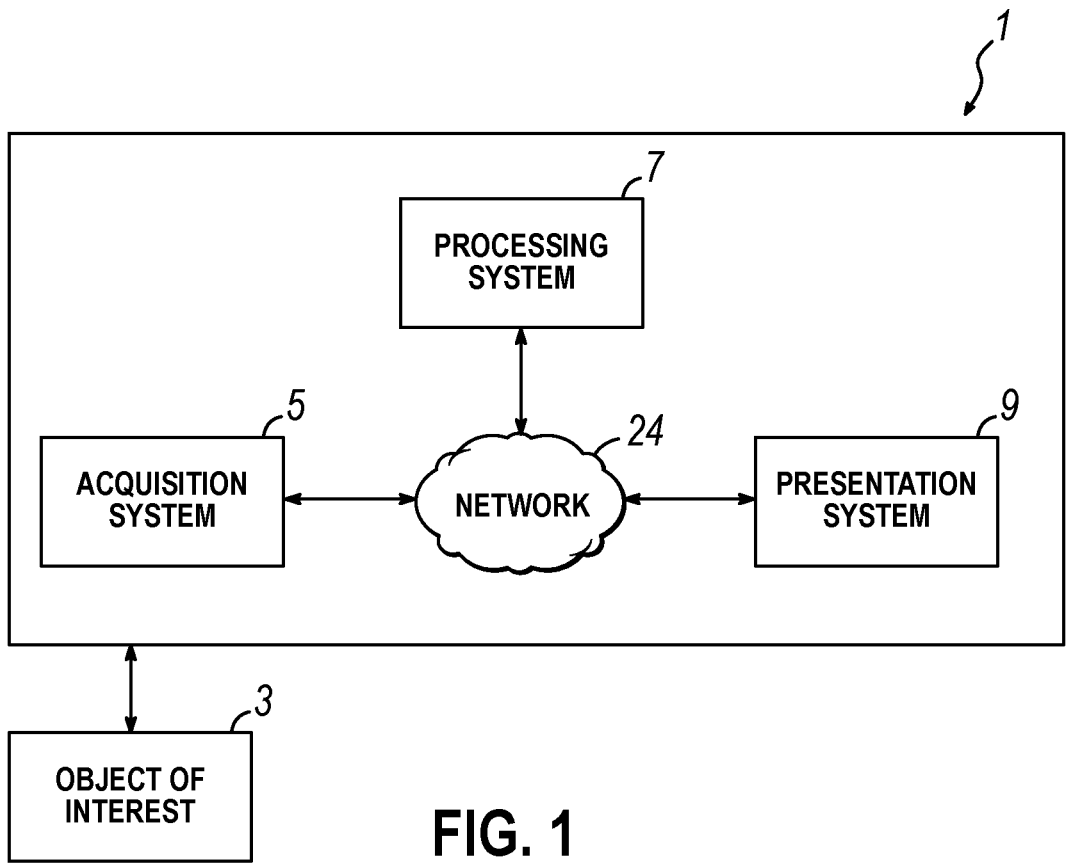
FIG. 1 depicts a diagrammatic view of an exemplary operating environment of an exemplary intraoral scanning system for use with an intraoral dental object of interest, including an acquisition system, a processing system, and a presentation system in communication with one another via a network.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Some versions of the present invention are directed to a scanning system comprising a plurality of patterns, wherein each pattern is based at least in part on traversing a hypercube graph or a Fibonacci cube graph using a Hamiltonian path; an acquisition system configured to illuminate an intraoral dental object of interest, hereinafter "object of interest," with at least one selected pattern from the plurality of patterns and record a patterned image reflected off the object of interest; a processing system configured to convert the patterned image into a three-dimensional model; and a presentation system configured to present the three-dimensional model.

Some versions of the present invention are directed to a method of scanning an object comprising creating a pattern based on a Hamiltonian path traversal of a hypercube graph or a Fibonacci cube graph; illuminating an object of interest with the pattern; recording a patterned image reflected off the object of interest; converting the patterned image into a three-dimensional model; and presenting the three-dimensional model on a visual display.

I. INTRAORAL SCANNING SYSTEM

As shown in FIG. 1, some versions of the present invention may be depicted as an intraoral scanning system (1) configured to acquire three-dimensional digital images of an object of interest (3) such as teeth, bite, or gingival structure. Some versions of intraoral scanning system (1) may include an acquisition system (5). Acquisition system (5) is generally configured to project pre-determined light patterns with error correction features onto object of interest (3) and capture the resulting reflected images. Some versions of intraoral scanning system (1) may include a processing system (7). Processing system (7) is generally configured to reconstruct the three-dimensional shape and color of at least a portion of object of interest (3) based on the reflected images captured by acquisition system (5). Intraoral scanning system (1) may further include a presentation system (9). Presentation system (9) is generally configured to display the reconstructed three-dimensional shape of object of interest (3) to a user.

In some versions of intraoral scanning system (1), acquisition system (5), processing system (7), and/or presentation system (9) may send and receive communications between one another directly. Some versions of intraoral scanning system (1), acquisition system (5), processing system (7), and/or presentation system (9) may send and receive communications between one another indirectly through a network (24). Network (24) may include one or more private or public networks (e.g. the Internet) that enable the exchange of data.

A. Exemplary Computer System

Figure 2:
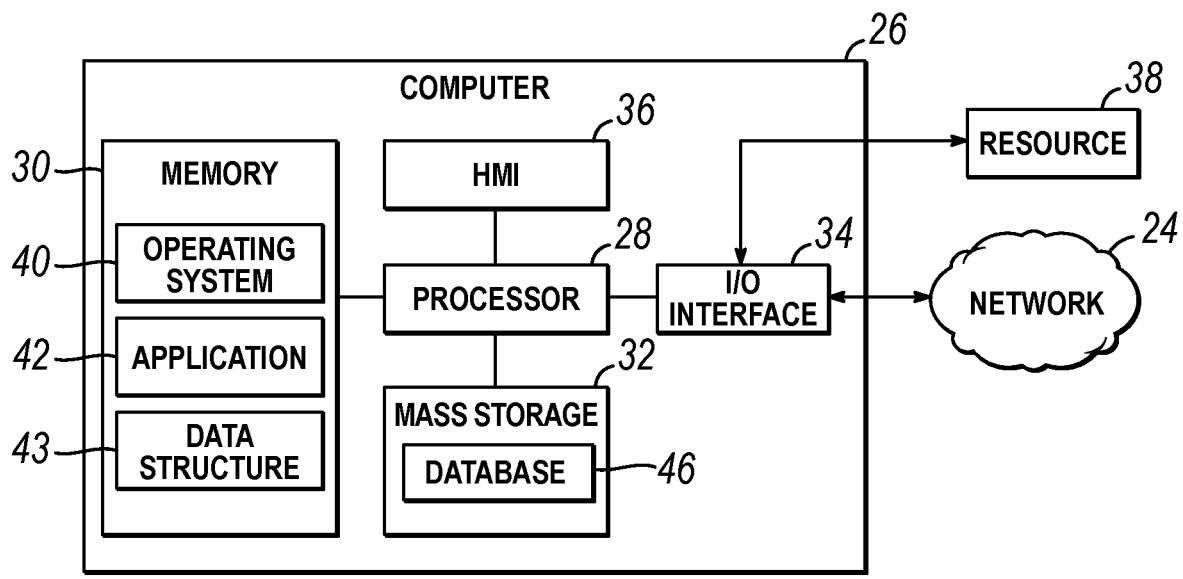
FIG. 2 depicts a diagrammatic view of an exemplary computer system of the intraoral scanning system of FIG. 1.

Referring now to FIG. 2, acquisition system (5), processing system (7), presentation system (9), and network (24) of intraoral scanning system (1) may incorporate therein or be implemented on one or more computing devices or systems, such as an exemplary computer system (26). Computer system (26) may include a processor (28), a memory (30), a mass storage memory device (32), an input/output (I/O) interface (34), and a Human Machine Interface (HMI) (36). Computer system (26) may also be operatively coupled to one or more external resources (38) via network (24) or I/O interface (34). External resources may include, but are not limited to, servers, databases, mass storage devices, peripheral devices, cloud-based network services, or any other suitable computer resource that may used by computer system (26).

Processor (28) may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in memory (30). Memory (30) may include a single memory device or a plurality of memory devices including, but not limited, to read-only memory (ROM), random access memory (RAM), volatile memory, non-volatile memory, static random access memory (SRAM), dynamic random access memory (DRAM), flash memory, cache memory, or any other device capable of storing information. Mass storage memory device (32) may include data storage devices such as a hard drive, optical drive, tape drive, non-volatile solid-state device, or any other device capable of storing information.

Processor (28) may operate under the control of an operating system (40) that resides in memory (30). Operating system (40) may manage computer resources so that computer program code embodied as one or more computer software applications, such as an application (42) residing in memory (30), may have instructions executed by processor (28). In an alternative embodiment, processor (28) may execute the application (42) directly, in which case operating system (40) may be omitted. One or more data structures (44) may also reside in memory (30), and may be used by processor (28), operating system (40), or application (42) to store or manipulate data.

I/O interface (34) may provide a machine interface that operatively couples processor (28) to other devices and systems, such as network (24) or external resource (38). Application (42) may thereby work cooperatively with network (24) or external resource (38) by communicating via I/O interface (34) to provide the various features, functions, applications, processes, or modules comprising embodiments of the invention. Application (42) may also have program code that is executed by one or more external resources (38), or otherwise rely on functions or signals provided by other system or network components external to computer system (26). Indeed, given the nearly endless hardware and software configurations possible, persons having ordinary skill in the art will understand that embodiments of the invention may include applications that are located externally to computer system (26), distributed among multiple computers or other external resources (38), or provided by computing resources (hardware and software) that are provided as a service over network (24), such as a cloud computing service.

HMI (36) may be operatively coupled to processor (28) of computer system (26) in a known manner to allow a user to interact directly with computer system (26). HMI (36) may include video or alphanumeric displays, a touch screen, a speaker, and any other suitable audio and visual indicators capable of providing data to the user. HMI (36) may also include input devices and controls such as an alphanumeric keyboard, a pointing device, keypads, pushbuttons, control knobs, microphones, etc., capable of accepting commands or input from the user and transmitting the entered input to processor (28).

A database (46) may reside on mass storage memory device (32), and may be used to collect and organize data used by the various systems and modules described herein. Database (46) may include data and supporting data structures that store and organize the data. In particular, database (46) may be arranged with any database organization or structure including, but not limited to, a relational database, a hierarchical database, a network database, or combinations thereof. A database management system in the form of a computer software application executing as instructions on processor (28) may be used to access the information or data stored in records of database (46) in response to a query, where a query may be dynamically determined and executed by operating system (40), other applications (42), or one or more modules.

B. Imaging Objects of Interest

As discussed above, intraoral scanning system (1) is generally configured to capture digital images of object of interest (3) whereby those images may be used to create a digital three-dimensional surface structure model of object of interest (3) for use and manipulation by a user. Specifically, in the dentistry context, intraoral scanning system (1) may be used to capture images of a patient's teeth and gingival structure and project a digital three-dimensional image of the teeth and gingival structure to a dentist for use and manipulation in treating the patient.

Figure 3:
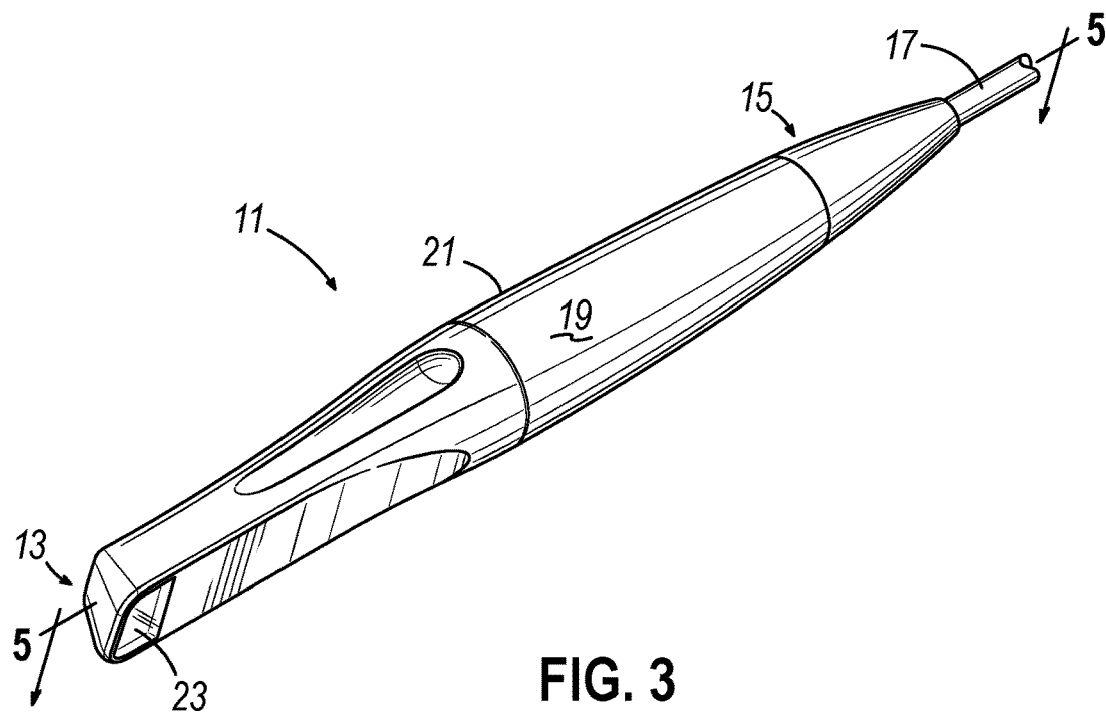
FIG. 3 depicts a perspective view of an exemplary scanning wand of the intraoral scanning system of FIG. 1.

As shown in FIGS. 3 and 5, intraoral scanning system (1) may include a scanning wand (11). Scanning wand (11) extends from a first end (13) to a second end (15), whereby a power and communication cable (17) may be attached. In other versions of scanning wand (11), communication cable (17) is absent and a wireless module (45) is incorporated within scanning wand (11) to provide for wireless data communication. A housing (19) extends from first end (13) to second end (15) and includes a handle portion (21) disposed at generally the midpoint for use in manual grasping by a user. An observation window (23) is defined in housing (19) at first end (13) and may include a transparent cover (not shown).

Figure 4:
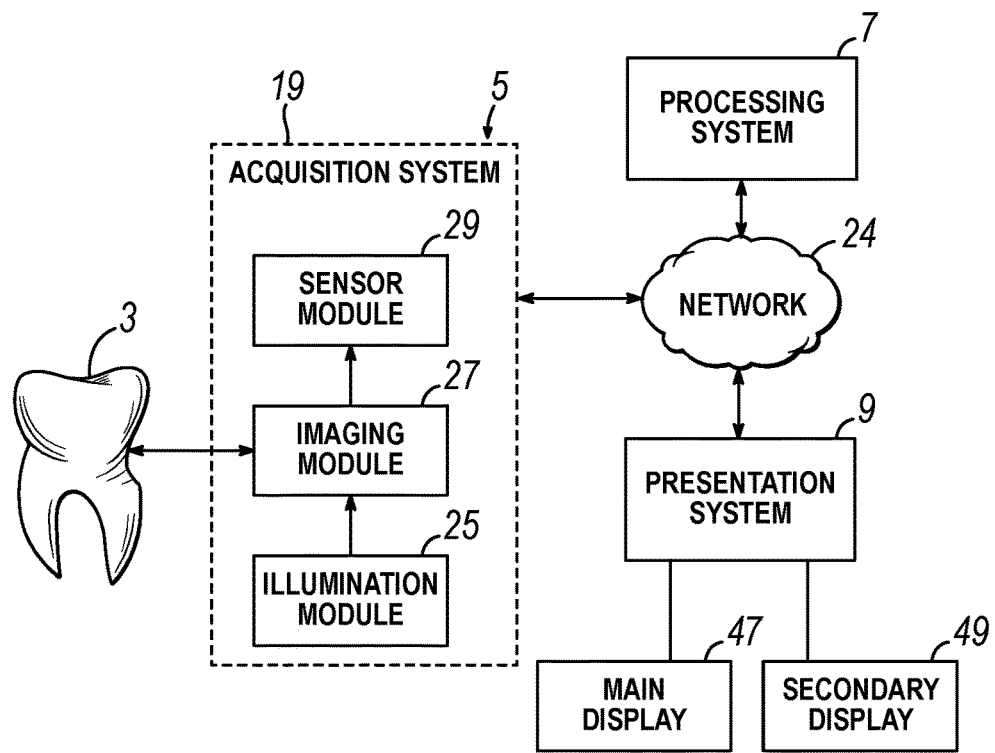
FIG. 4 depicts a schematic view of an exemplary illumination module, an exemplary imaging module, an exemplary sensor module of the acquisition system of FIG. 1.

As shown in FIG. 4, in some versions of intraoral scanning system (1), some or all of the features or functionalities of acquisition system (5) are associated with scanning wand (11). Scanning wand (11) may include various circuitry and/or elements described with respect to computing system (26) to allow various modules to perform some or all of the various processing and computing functions of acquisition system (5). More specifically, acquisition system (5) may include an illumination module (25), an imaging module (27), and/or a sensor module (29) to facilitate projecting light patterns onto object of interest (3) and capturing the resulting reflected images for further downstream processing. As described herein, illumination module (25), imaging module (27), and sensor module (29) are exemplary modules and the associated features and methods described herein may be distributed or encapsulated by other modules, software objects, and/or circuitry within intraoral scanning system (1) without departing from the spirit of the disclosure.

i. Illumination Module

As shown in FIG. 5, illumination module (25) may include a light source (31) and a light modulator (33) for manipulating the light projected via light source (31) into a plurality of coded light patterns matching those generated via graph theoretic methodologies described in greater detail below. Illumination module (25) may include a memory such as memory (30) for storing a data set representing the plurality of coded light patterns. The data representing a particular coded light pattern is thereby selected and passed to light modulator (33) for creating the desired coded light pattern, which is thereby presented and/or transmitted to imaging module (27).

For example, illumination module (25) or a processor associated therewith may select data associated with a particular coded light pattern and actuate light modulator (33) in accordance with selected data to project the selected coded light pattern. In some versions of light modulator (33), this actuation is manifested by angling or turning a series or grid of micro-mirrors within light modulator (33) whereby the desired coded light pattern is projected along a light pathway when illuminated by light source (31). Light modulator (33) may take the form of spatial or temporal light modulation. Light modulator (33) may comprise a digital light processing (DLP) element or a digital micromirror device (DMD). Some versions of light modulator (33) are adaptable and reconfigurable via software before or during a scanning procedure.

Once the known coded light pattern is projected and reflected back into acquisition system (5), digital models of the scanned object of interest (3) are built and provided to the user. Inasmuch as unencoded general beams of light result in poor reflection on objects such as teeth, coded light beams such as a black and white checkerboard grid pattern are used. The features of the projected coded light patterns are known prior to projection. Therefore, any bending or warping of the projected coded light patterns are associated with three-dimensional features of object of interest (3) and recreated spatially in the digital model of object of interest (3).

ii. Imaging Module

As shown in FIGS. 3-5, the desired coded light pattern is transmitted from illumination module (25) to imaging module (27), whereby it is focused and tuned by a lens assembly (35) for efficient projection and imaging capture with respect to object of interest (3). Lens assembly (35) includes a varifocal lens (37) operably connected to an actuation element (39). Varifocal lens (37) may be dynamically adjusted during scanning to focus and tune the projected light patterns as needed by changing the index of refraction of the lens. Actuation element (39) facilitates the dynamic adjustment of varifocal lens (37) by varying an electric current gradient or an acoustic gradient associated with actuation element (39) to change the index of refraction. In some versions of intraoral scanning system (1), varifocal lens (37) is non-mechanically adjustable for varying the focal length of the underlying lens.

Variation in the depth of focus of conventional lenses constructed from crystalline materials such as optical glass typically requires the automatic or manual adjustment of location or size of mechanical elements. This may cause wear and tear due to increased friction; cause increased power consumption; require a bulkier optical design; cause diffraction effects at smaller apertures; and drastically slow down the imaging system. These factors limit the efficacy of optical elements requiring mechanical actuation in dynamic, limited working-space applications such as intraoral scanning.

In some versions of intraoral scanner (1), varifocal lens (37) is comprised of a shape-memory polymer, also referred to as a shape-changing polymer. Shape-memory polymers may be controllably shaped and reshaped in the presence of external stimuli such as heat, light, and/or pressure. In some versions of varifocal lens (37), a varifocal liquid is filled with one optical fluid of known refractive index and is sealed off with an elastic shape-memory poly membrane. Electric current flowing through a voice coil of an electromagnetic actuator causes pressure variation which in turn modifies the curvature of shape-memory polymer membrane, which in turn modifies the focal length of varifocal lens (37). Current-driven actuation of varifocal lens (37) allows operation at lower voltages, resulting in a large range of operational apertures. This, in turn, results in a faster imaging system with some versions of varifocal lens (37) providing sub-microsecond focal length adjustments.

Figure 7A:
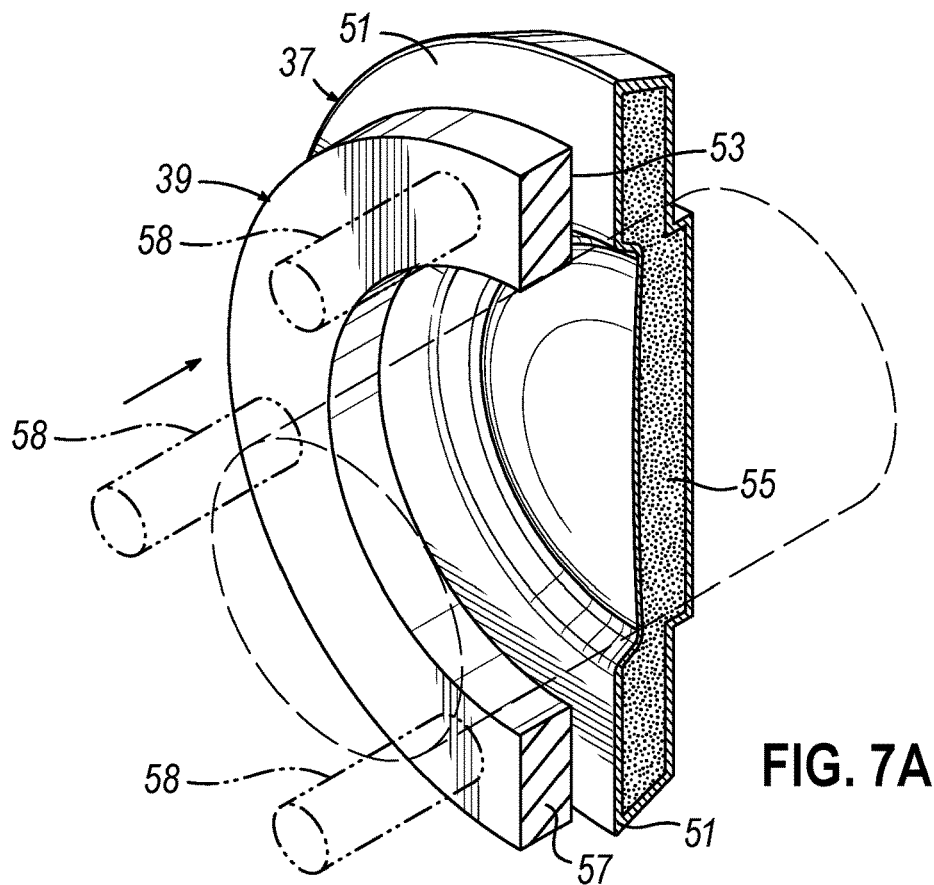
FIG. 7A depicts a perspective view of an exemplary varifocal lens in a first position for use by the imaging module of FIG. 4.
Figure 7B:
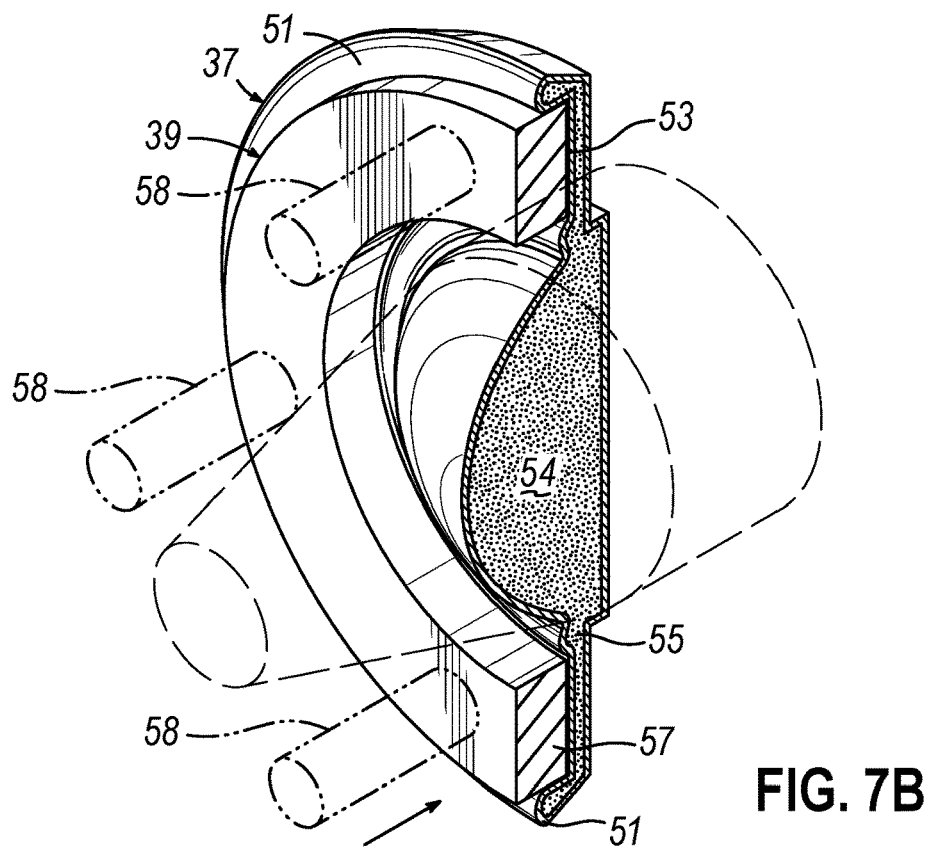
FIG. 7B depicts a perspective view of the varifocal lens of FIG. 7A in a second position.

An exemplary varifocal lens (37) and actuation element (39) are depicted in FIGS. 7A and 7B, with FIG. 7A depicting varifocal lens (37) and actuation element (39) in a first orientation, and FIG. 7B depicting varifocal lens (37) and actuation element (39) in a second orientation. Some versions of varifocal lens (37) includes a membrane (49) having a generally flat, arcuate, actuation surface (53). Membrane (49) may be formed from a shape-memory polymer with a default position shown in FIG. 7A. Membrane (49) defines a fluid pocket (54). Fluid pocket (54) contains an effective amount of a fluid (55) having a known refractive index therein.

Some versions of actuation element (39) include a voice coil actuator (57), bonded to actuation surface (53) of membrane (49). When a current is applied to voice coil actuator (57), voice coil actuator (57) varies the pressure on membrane (49) by pressing against or releasing from actuation surface (53). The pressure changes within membrane (49) act on fluid pocket (54), changing the overall shape of fluid pocket (54), which in turn changes the focal length of varifocal lens (37) and adjusting the focus. With particular reference to FIG. 7A, when varifocal lens (37) and actuation element (39) are in the first orientation, fluid pocket (54) is generally flat and planer due to voice coil actuator (57) providing a minimal amount of pressure on actuation surface (53) and a particular amount of fluid (55) within the pathway of the light beam passing therethrough.

As current is applied to voice coil actuator (57), voice coil actuator (57) presses against actuation surface (53), which increases pressure within fluid pocket (54) due to squeezing the outer rim of membrane (51). This in turn swells and balloons the generally planer nature of fluid pocket (54) as varifocal lens (37) and actuation element (39) move into the second orientation. In the second orientation, the overall shape of fluid pocket (54) is changed such that more fluid (55) is disposed within the pathway of the outgoing light beam, thereby changing the overall focus of the light beam as compared to the first orientation. While varifocal lens (37) and actuation element (39) is shown in two orientations, one will readily understand that any orientation between the first and second orientation provide a different overall focus for the light beam and there exists a large amount of intermediate focal orientations for varifocal lens (37) achieved by varying the current applied to voice coil actuator (47).

Rather than direct actuation of voice coil actuator (57), another element may be used to press against voice coil actuator (57) to actuate varifocal lens (37). As shown in FIGS. 7A and 7B, an actuation rod (58) is shown in phantom to depict an actuation element pressing against voice coil actuator (57). Actuation rod (58) is depicted for exemplary purposely only. Any other style or shape of element may be used to actuate varifocal lens (37).

In other versions of varifocal lens (37), the focal length may be varied without modifying the curvature of the underlying lens. In these versions, actuation element (39) incorporates acoustic waves to increase or decrease the local density of an optical fluid within a pocket similar to fluid pocket (54), which in turn increases or decreases the local index of refraction within the optical fluid. Thus, custom index of refraction profiles throughout varifocal lens (37) are thereby created using sound. As the index of refraction modulation involves no lens curvature changes, high speed sub-microsecond focal length adjustments can be accomplished using this approach, resulting in a fast imaging system.

With respect to feedback regarding focusing and adjusting varifocal lens (37) of lens assembly (35), various focal sharpness and distance sensing features may be provided within any one of illumination module (25), imaging module (27), and sensor module (29). However, these features will be discussed in greater detail below with respect to sensor module (29).

iii. Sensor Module

As shown in FIG. 4, a coded light pattern is projected toward object of interest (3) and a reflected image of this potentially deformed light pattern overlaid on object of interest (3) is reflected to imaging module (27). At this stage, image module (27) may optionally apply image processing operations to the reflected image such as cropping, rotating, translating, reflecting, and similar operations. Image module (27) thereafter passes the reflected image to an image sensor (41) of sensor module (29). Image sensor (41) includes elements for receiving the reflected image and converting the optical/light stream into digital data. Some versions of image sensor (41) include a CMOS camera element, a CCD camera element, or any other element for converting light into electrons. Converting the reflected image light into electrons via image sensor (41) initiates the conversion into digital data to capture the images reflected off object of interest (3) through imaging module (27).

Other versions of image sensor (41) may include a light field camera or a plenoptics camera. Unlike conventional two-dimensional sensors that integrate light intensities reflected from different points of the object of interest, light field or plenoptic cameras preserve both light field intensity and direction of the reflected rays. Alternatively, an array of micro-lenses may be used in front of image sensor (41) to compute light fields. However, the array of micro-lenses may require expensive and careful construction of the sensitive lens array optical elements. Thus, some versions of sensor module (29) may include a coded mask (43), rather than an array of micro-lenses, in front of image sensor (41).

As shown in FIGS. 5 and 6, coded mask (43) is disposed in front of image sensor (41) and effectively frequency modulates the incoming reflected spatially multiplexed images. These reflected images can then be frequency demodulated to create a multi-depth plane digital image. In some versions, coded mask (43) may include an arrangement of pinhole apertures (48). The arrangement of pinhole apertures (48) may be a pseudorandom arrangement or a deterministic arrangement.

Image sensor (41) may also be operatively connected to lens assembly (35) with logic circuitry to determine whether an incoming reflected image is out of focus and provide a feedback control signal to lens assembly (35) to fine tune varifocal lens (37). In some versions of intraoral scanning system (1), image sensor (41) provides a focusing offset along with a notification the incoming reflected image is out of focus. For example, if image sensor (41) receives the incoming reflected image and determines the image is slightly unfocused or blurry in certain areas such as the periphery and determines the lens should be "zoomed out" three millimeters, image sensor (41) signals to lens assembly (35) the image is out of focus along with a correction offset of +3 mm. This correction offset is thereafter used by lens assembly (35) to refocus varifocal lens (37) three millimeters deeper using actuation element (39) by actuating actuation element (39) accordingly. Some versions of this feedback loop regarding the focus of varifocal lens (37) complete the loop in less than a microsecond, such that varifocal lens (37) is constantly adjusting in essentially real time regardless of whether the user maintains scanning wand (11) at a fixed distance from object of interest (3).

iv. Processor System

After receiving the captured images reflected off object of interest (3) and converting these images to digital data, sensor module (29) communicates the digitized reflected image data to processor system (7). Processor system (7) may be embedded in a mobile computing cart (not shown) for bi-directional exchange of data. In those versions of intraoral scanner (1) with a wired data connection, data is exchanged between sensor module (29) and processor system (7) via cable (17). In those versions of intraoral scanning system (1) with a wireless data connection, data is exchanged between sensor module (29) and processor system (7) via wireless module (45) disposed in scanning wand (11).

In some versions of intraoral scanning system (1), processor system (7) decodes the image captured by sensor module (29) to create depth disparity maps. The depth maps are used to construct a point cloud representation of the shape of object of interest (3). In practice, multiple point clouds would need to be generated to cover the entire volume of object of interest (3). In some versions of intraoral scanning system (1), an iterative closest point algorithm is used to register a set of point clouds to form a unified point cloud representing the entirety of object of interest (3). Once these displayable forms of the captured object of interest (3) are generated by processor system (7), the final models and images are communicated to presentation system (9) for display to a user.

v. Presentation System

As shown in FIG. 4, presentation system (9) is configured to receive information regarding the display of object of interest (3) and provide this visual information to a user. In some versions, presentation system (9) comprises a main display (47). Main display (47) may comprise a desktop monitor, a laptop display, or a handheld smartphone or tablet. A user may view, turn, zoom in and out, an otherwise generally interact with the displayed model of object of interest (3) via presentation system (9) on main display (47).

Current medical scanning procedures, such as intraoral scanning in a dental office, requires practitioners to rapidly switch their field of vision back and forth from the patient to a computer or monitor display providing real-time feedback. This decreases the efficiency of the procedure and increases the time overhead both for the patient and practitioner. To address these issues, some versions of presentation system (9) may include a secondary display (49) to supplement main display (47).

Secondary display (49) may comprise a headset, eyeglasses, contacts, or similar elements and provide to the user augmented reality (AR), virtual reality (VR), mixed reality (MR), or any similar technology. In some versions of headset (47), the user may interact with headset (47) via voice controls, hand gestures, or eye blinks.

Secondary display (49) may be configured to provide contextual information to the user by gathering information from the procedure environment and adding it to the user's field of view. This added information allows the user to continue the procedure without shifting their gaze or attention from the patient and/or object of interest (3). For example, in an intraoral scanning application, secondary display (49) may illustrate the real-time three-dimensional reconstruction of the dental arch providing feedback to the practitioner. Secondary display (49) may also provide real-time information on the optimal path of scanning wand (11) movement based on the status of the procedure. As a way of example, using secondary display (49), the practitioner may also be able to visualize a semantic segmentation overlay of the tooth surfaces of interest and evaluate a plurality of dental implant approaches on the site of interest prior to the graft.

In some versions of processing system (7), secondary display (49) may be used to provide immersive training to practitioners without the need for a study patient. By way of example, dental practitioners may practice virtual intraoral scanning or restorative dentistry procedures without a patient. This can lead to a quicker pace of learning without adversely affecting clinical output.

C. Coded Light Patterns Based on Path Traversal

As referenced above with respect to illumination module (25), coded light patterns (also known as "structured light") are projected onto object of interest (3) to aid in determining the three-dimensional features of the underlying object. Objects of interest (3) such as teeth are poorly reflective and possibly include stains or other inconsistencies regarding surface reflectiveness. Thus, unencoded light beams can only provide a limited understanding of the three-dimensional features of the teeth. Projecting a known pattern (often grids or horizontal bars) on to a scene allows the pattern to deform when striking surfaces. This deformation allows vision/sensor systems to calculate the three-dimensional depth and surface information of object of interest (3).

Coded light patterns can be single-shot, where a single coded image is projected, or multi-shot, where multiple coded time-multiplexed images are projected. Single-shot methods are well suited for dynamic high-speed applications but assume smooth local variations in the depth of the scene to be reconstructed. This limits the efficacy of single-shot methods in intraoral applications where the surface of a tooth of interest may have several sharp edges and discontinuities that violate this assumption.

There are several time-multiplexed pattern generation techniques, such as Gray coding and Sinusoidal Phase Shift projection. The Gray coding technique is not suitable for high speed applications. Sinusoidal Phase Shift projection is widely used but susceptible to noise due to pixel crosstalk, which makes the acquired reflected images more difficult to process and prone to error.

Pattern coding schemes can be "discrete" or "continuous." In discrete coding schemes, the intensities of patterns are picked from a discrete set. Discrete coding approaches such as binary or N-ary Gray coding require several time-multiplexed patterns to be projected on the object of interest for achieving higher resolution. Typically, the number of patterns required is proportional to the log base N of the number of encoded regions. There are several other discrete coding approaches known in the art that use color or monochrome de Brujin sequences and M-arrays. All discrete approaches suffer in low albedo situations and when the shade of the object surface (e.g. stains on teeth) may interfere with the chroma interpretation of the reflected beam.

Continuous coding schemes can achieve subpixel resolution and require projection of fewer images in comparison to discrete coding approaches. The most widely used structured light technique in the art is the continuous coding approaching involving Sinusoidal Phase Shift.

Rather than Sinusoidal Phase Shift, intraoral scanning system (1) incorporates a time-multiplexed pattern generation technique using Hamiltonian paths to traverse graphs to generate the underlying coded patterns. Compared to conventionally generated patterns, the pattern of codes generated from the present approach utilizing Hamiltonian path traversal has properties that make it significantly more robust to noise and minimization of pixel crosstalk. In some version of intraoral scanning system (1), the code patterns are formed by traversing a Hamiltonian path on a hypercube graph. In other versions of intraoral scanning system (1), the code patterns are formed by traversing a Hamiltonian path on a Fibonacci cube graph.

Intraoral scanning system (1) is configured to generate a plurality of coded patterns in accordance with the disclosed methods herein, prior to a scanning session. After generation, the plurality of coded patterns are stored within illumination module (25), retrieved, and projected as needed by intraoral scanning system (1).

Figure 8:
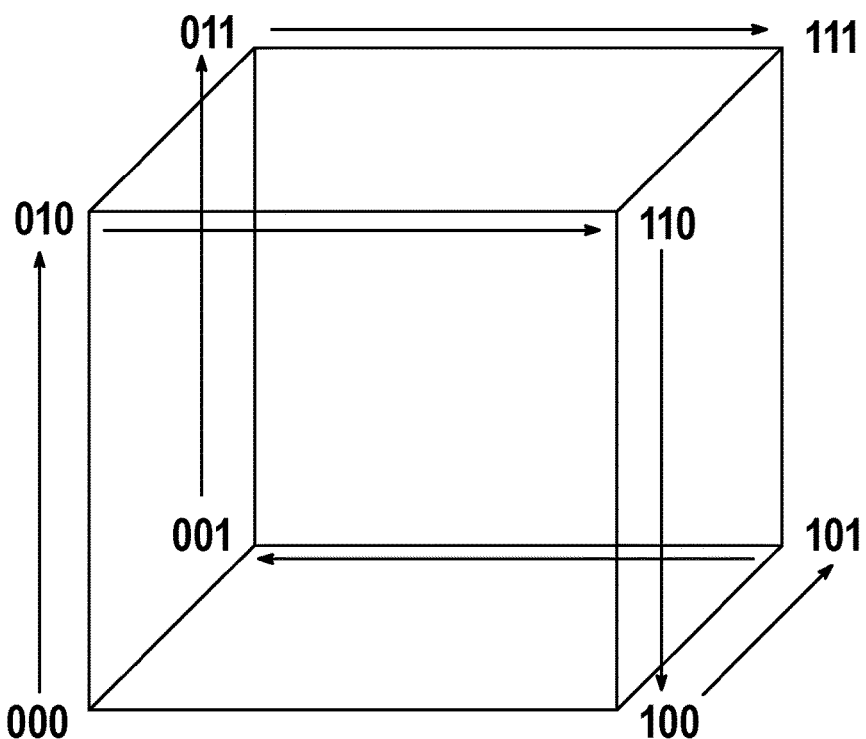
FIG. 8 depicts a perspective view of an exemplary hypercube and an exemplary Hamiltonian path traversal thereof.
Figure 10:
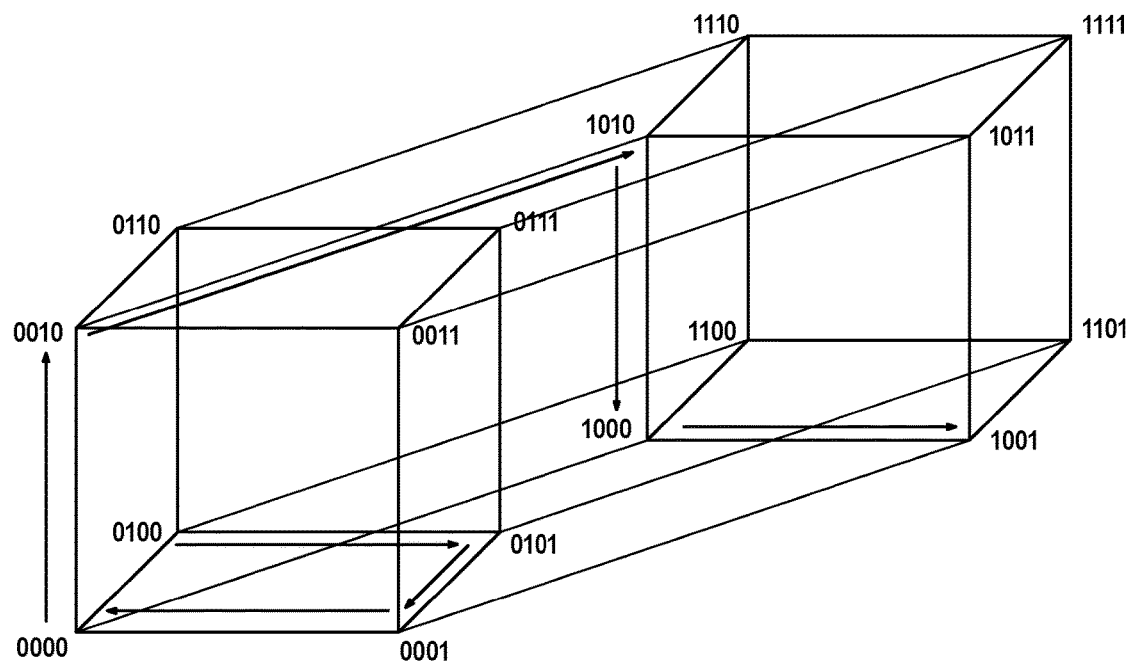
FIG. 10 depicts a perspective view of an exemplary Fibonacci cube graph as a subgraph of a Hypercube graph and an exemplary Hamiltonian path traversal thereof.

A hypercube is an x-dimensional analogue of a square (x=2) and a cube (x=3). It is a closed figure with edges and vertices. FIG. 8 depicts a "3-cube" hypercube having eight vertices and twelve edges. FIG. 10 depicts a "4-cube" hypercube having sixteen vertices and thirty-two edges.

Thus, a hypercube graph $Q_n$ is composed of $n(2n-1)$ edges and $2n$ vertices with $n$ edges incident to each vertex. If each vertex of a $Q_n$ hypercube graph is represented by a unique n-bit binary string representation, then any vertex in $Q_n$ shares an edge either another vertex in $Q_n$ if and only if they differ by 1 bit in their n-bit binary string representations (i.e. Hamming distance between any two adjacent pair of vertices is one). A Hamiltonian path on a hypercube graph $Q_n$ is defined as any path traversed on $Q_n$ that visits all vertices of $Q_n$ exactly once. The coding curve length of a Hamiltonian path is $2^n-2$ if n is odd and $2^n-4$ if n is even. This is larger than the coding path length of the widely used phase-shift sinusoidal fringe projection technique which has a path length of $\pi n^{0.5}/2 \cdot 2^{0.5}$.

A Fibonacci cube of order n, represented as $T_n$ is a family of undirected graphs with $F_{n+2}$ vertices, where $F_n$ is a Fibonacci number. The $F_{n+2}$ vertices are labeled by binary Zeckendorf representations such that no vertex has two consecutive 1's in their bit string representation. Every Fibonacci cube has a Hamiltonian Path. For example, in FIG. 10, a Fibonacci Cube Graph may be formed as a subgraph of $Q_4$ by traversing a Hamiltonian path along the vertices that have no two consecutive 1's in their binary representation exactly once.

A longer coding curve provide more robustness to measurement noise during decoding. In some versions of intraoral scanning system (1), Hamiltonian paths on hypercube graphs of $n>=3$ are traversed to derive pattern coding functions. Coding functions derived from this path are more robust to noise than traditional structured light techniques using phase-shifted sinusoidal fringe projection. Additionally, because the Hamming distance of adjacent vertices on a hypercube graph is 1, the vertices on the Hamiltonian path form a Gray code which further bestows the present coding functions with more robust error-correcting properties.

A $Q_3$ hypercube graph is represented in FIG. 8 having eight vertices and twelve edges. The pattern generation method of the present disclosure begins with assigning each of the eight vertices a binary representation of numbers 0-7, namely, 000, 001, 010, 011, 100, 101, 110, 111. The Hamiltonian path traversal begins with 000 and proceeds to traverse each vertex once, passing along an edge at most once. An alternative representation of this Hamiltonian path traversal is depicted in FIG. 9, with the changes in bits as the Hamiltonian path is traversed are noted with a line between the changing bits.

Figure 9:
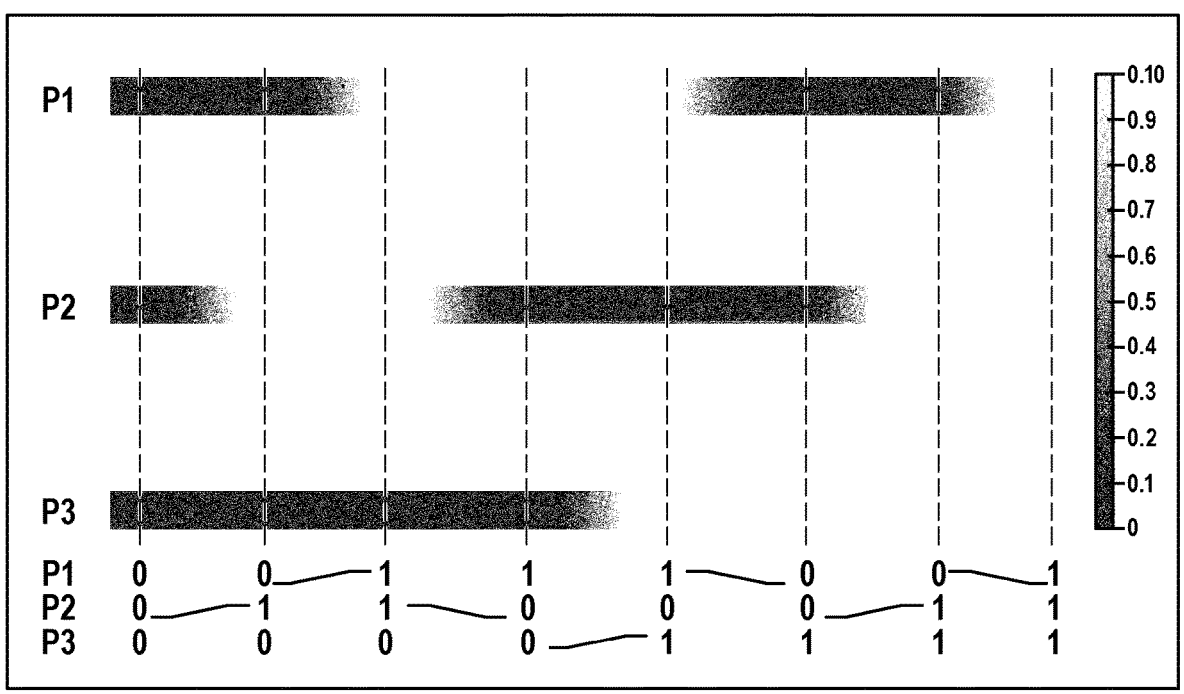
FIG. 9 depicts a diagrammatic view of three exemplary gradient ribbons for use by the intraoral scanning system of FIG. 1.

As shown in FIG. 9, creating a pattern from the graph traversal is achieved by assigning a particular color to a bit, and providing a gradient transition between bits as the graph traversal moves through the Hamiltonian path. For example, a 0 may be assigned "black" and a 1 may be assigned "white" and the transition or lack thereof between these colors may be assigned to each potential bit transition (i.e. 0 to 0; 1 to 0; 1 to 1; 0 to 1). In the example depicted in FIG. 9, 0 is assigned black and 1 is assigned white. Given this assignment, Table 1 depicts the following gradient transitions assigned to each bit transition:

TABLE 1

| Bit Transition | Gradient Transition |
| --- | --- |
| 0 to 0 | Black to black |
| 0 to 1 | Black to white |
| 1 to 0 | White to black |
| 1 to 1 | White to white |

Each path, at the bit level, may be tracked along each transition to form a gradient ribbon. These three separate paths corresponding to the three bits required to represent a $Q_3$ hypercube are shown in FIG. 9 as a gradient ribbon (P1), gradient ribbon (P2), and gradient ribbon (P3). The thickness of gradient ribbons (P1, P2, P3) is selected as needed, though a single pixel would be sufficient to represent the transitions. In some versions of intraoral scanning system (1), gradient ribbons (P1, P2, P3) are individually expanded by repeating itself horizontally to provide thickness to the gradient ribbon (P1, P2, P3). For example, if gradient ribbon (P1) is 1 pixel in height and 800 pixels in length, gradient ribbon (P1) may be repeated horizontally 400 times to create an 800×400 pixel size pattern for projection onto object of interest (3). Some versions of the coded patterns discussed above may comprise this 800×400 pixel pattern and those similar patterns generated from gradient ribbons (P1, P2, P3).

Some versions of intraoral scanning system (1) project gradient ribbon (P1), followed by gradient ribbon (P2), followed by gradient ribbon (P3) in a "scan burst" format to capture successive reflected images of a particular area quickly using different coded patterns in generally the same orientation of scanning wand (11). The multiple reflected images of the same area with different patterns are then utilized to determine the three-dimensional characteristics of the area. Similarly, bit-inverses of gradient ribbons (P1, P2, P3) may be created and projected in any sequence in any given scan burst to aid in determining the three-dimensional characteristics of the area.

Figure 11:
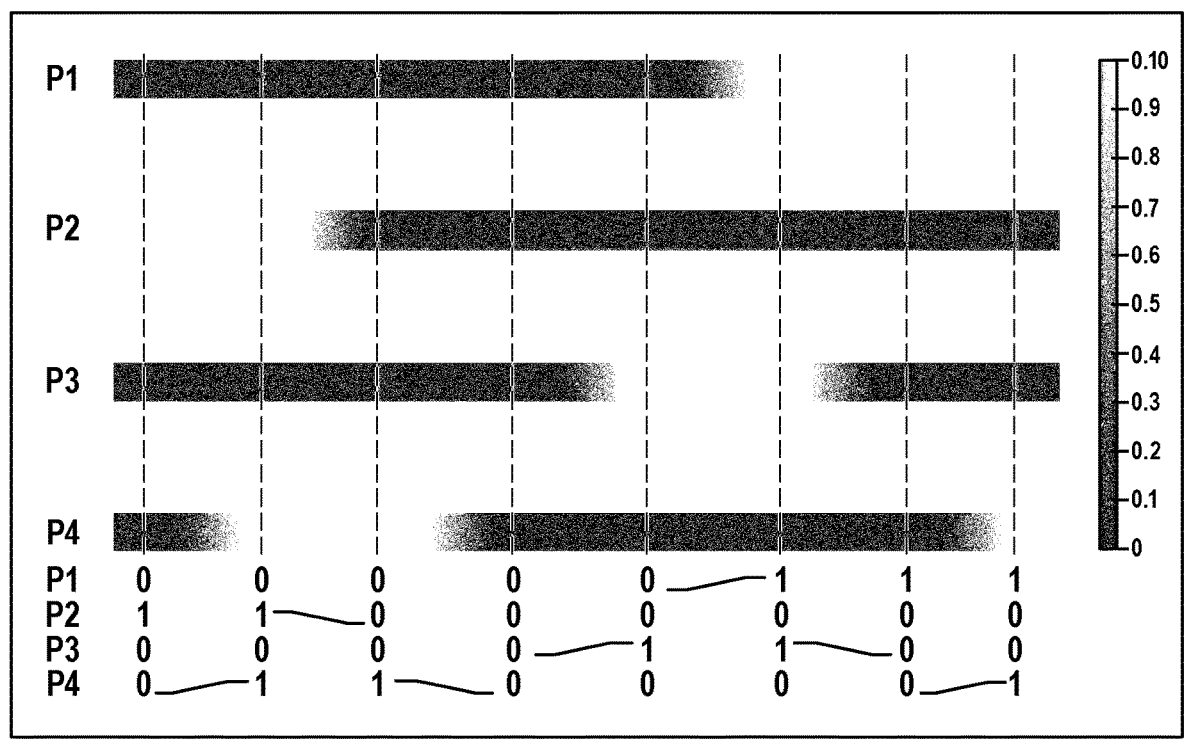
FIG. 11 depicts a diagrammatic view of four exemplary gradient ribbons for use by the intraoral scanning system of FIG. 1.

FIGS. 10 and 11 depict a similar structure with a Fibonacci cube graph induced as a subgraph of $Q_4$ and a similar Hamiltonian traversal. The Hamiltonian path traversal of the graph depicted in FIG. 10 is reflected in FIG. 11 with four gradient ribbons. These four gradient ribbons may be converted into four corresponding coded patterns and used to determine three-dimensional characteristics of object of interest (3) as described above.

II. INTRAORAL SCANNING METHOD

Figure 12:
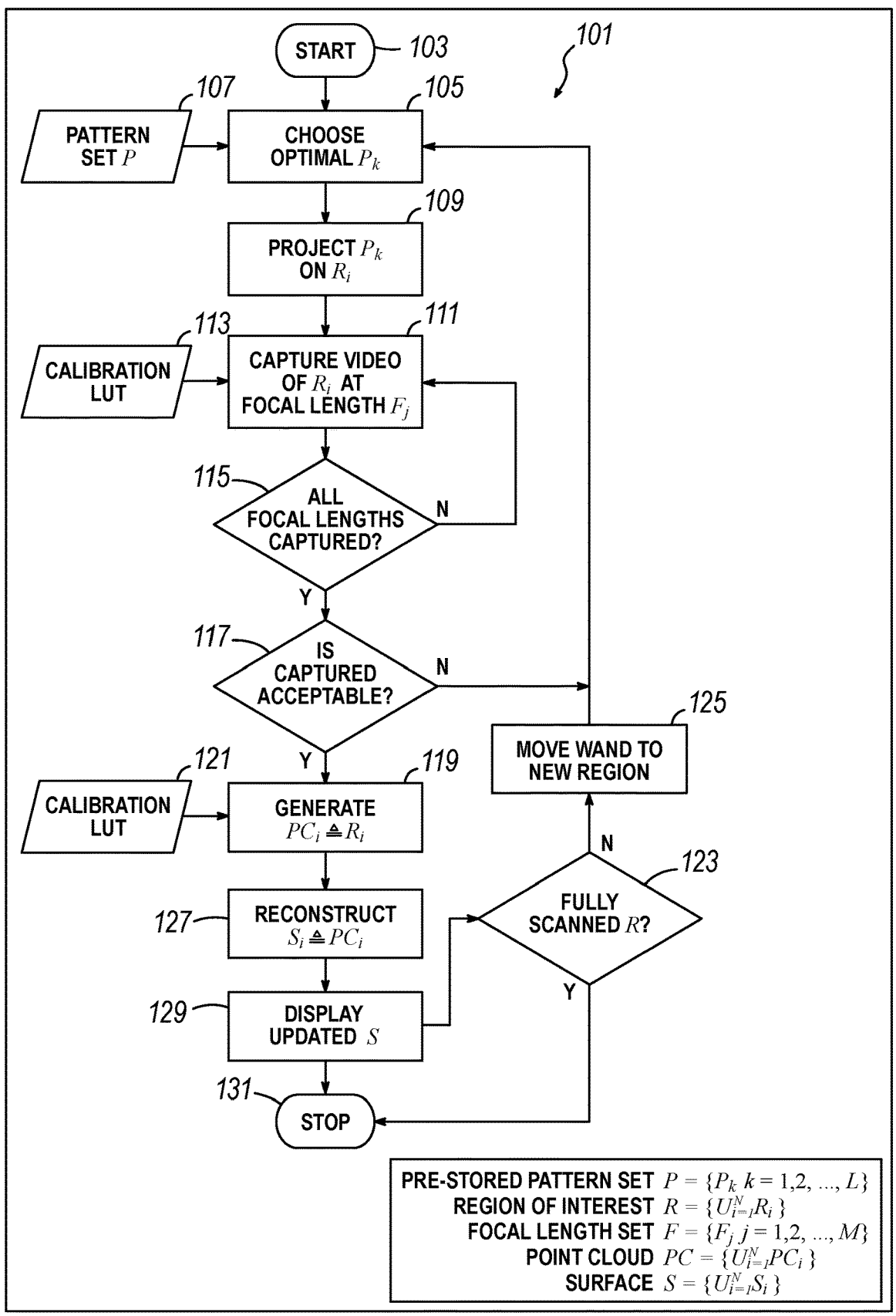
FIG. 12 depicts a flowchart representing an exemplary method used in the intraoral scanning system of FIG. 1.

As shown in FIG. 12, some versions of intraoral scanning system (1) may be depicted as an intraoral scanning method (101). Intraoral scanning method (101) is initiated with a step (103). Step (103) presupposes scanning wand (11) is proximate a region of interest ($R_i$) from a plurality of regions (R) along a complete surface (S) of object of interest (3). Once initiated with step (103), intraoral scanning method (101) proceeds to a step (105). In step (105), an optimal pattern ($P_k$) is selected from a pre-stored pattern set (P). Pre-stored pattern set (P) is generated and supplied to step (105) via a step (107). In some versions of intraoral scanning method (101), pre-stored pattern set (P) is generated prior to the initiation of step (103). The patterns within pre-stored pattern set (P) are generated by traversing hypercube graphs or Fibonacci cube graphs using the Hamiltonian path traversal methods described above. Once optimal pattern ($P_k$) is selected, step (105) proceeds to a step (109). In step (109), optimal pattern ($P_k$) is projected on region of interest ($R_i$). Thereafter, step (109) proceeds to a step (111).

In step (111), video and/or images of region of interest ($R_i$) are captured at a particular focal length ($F_j$) of varifocal lens (37) selected from a set of focal lengths (F). A step (113) may be incorporated into method (101), whereby a calibration lookup table (LUT) is provided to refine and aid in the specification of set of focal length (F). The calibration LUT helps associate the geometry of the illumination module and the varifocal capture of the imaging and sensor module. Thereafter, step (111) proceeds to a step (115). Step (115) determines whether all focal lengths within set of focal lengths (F) have been captured with respect to optimal pattern ($P_k$) and region of interest ($R_i$). If step (115) determines all focal lengths within set of focal length (F) have been captured with respect to optimal pattern ($P_k$) and region of interest ($R_i$), step (115) proceeds to a step (117). Conversely, if step (115) determines that not all focal lengths within set of focal lengths (F) have been captured with respect to optimal pattern ($P_k$) and region of interest ($R_i$), step (115) proceeds back to step (111).

In step (117), intraoral scanning method (101) determines whether the capture of region of interest ($R_i$) is acceptable. The designation of "acceptable" within step (117) is dynamic with respect to the scanning intent, deliverable, and/or object of interest (3). In some version of intraoral scanning method (101), an acceptable capture of region of interest ($R_i$) is determined by ascertaining the quality of one or more of the following: image focus, image contrast, image glare (such as caused by excess saliva or metallic restorations during intraoral scanning), soft tissue interference (such as operator fingers or patient tongue during intraoral scanning). If step (117) determines the capture of region of interest ($R_i$) is acceptable, step (117) proceeds to a step (119). Conversely, if step (117) determines the capture of region of interest ($R_i$) is not acceptable, step (117) proceeds back to step (105) where a different pattern may be selected, whereby the progression of steps (105, 109, 111, 115, and 117) is repeated until the capture of region of interest ($R_i$) is determined to be acceptable.

In step (119), a point cloud ($PC_i$) is generated based on the images captured for the region of interest ($R_i$). The projected patterns ($P_k$) from the pre-stored pattern set (P) and captured reflected images are analyzed and used to determine the three-dimensional shape of the region of interest ($R_i$). This shape is reflected in point cloud ($PC_i$). A step (121) may be incorporated into method (101), whereby a calibration lookup table (LUT) is provided to refine and aid in the generation of point cloud ($PC_i$). The calibration LUT may be invoked at this point to determine the appropriate relative geometry of the illumination and sensor and imaging module during acceptable capture and used to inform the point cloud generation. Once point cloud ($PC_i$) is generated, step (119) proceeds to a step (127).

The complete surface (S) of object of interest (3) includes a surface ($S_i$) correlating to region of interest ($R_i$). In step (127), surface ($S_i$) is reconstructed using point cloud ($PC_i$). In some versions of method (101), a polygonal mesh generation is performed in step (127) to represent the underlying teeth structure. This polygonal mesh may be the expected output of method (101). Thereafter, step (127) proceeds to step (129).

In step (129), the user display depicting complete surface (S) of object of interest (3) is updated with the information regarding surface ($S_i$). This provides the user a current view of complete surface (S) with the most current information regarding surface ($S_i$) at region of interest ($R_i$). Any "holes" in the dataset or omissions within complete surface (S) will be displayed to the user via a lack of surface features or some other visual indication. Thereafter, the user may move scanning wand (11) to a new region of interest to acquire the missing data. After step (129), method (101) moves to a step (123).

In step (123), a determination is made regarding whether region (R) containing region of interest ($R_i$) is fully scanned. If region (R) containing region of interest ($R_i$) is not fully scanned, step (123) proceeds to step (125). In step (125), scanning wand (11) is moved or repositioned to a new region of interest ($R_i$) within region (R) and step (125) proceeds back to step (105). Conversely, if region (R) containing region of interest ($R_i$) is fully scanned, step (123) proceeds to a step (131) whereby method (101) ends.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An intraoral dental scanning system comprising: (a) a plurality of patterns, wherein each pattern is based at least in part on a Hamiltonian path traversal of a graph; (b) an acquisition system configured to illuminate an intraoral dental object of interest with at least one selected pattern from the plurality of patterns and record a patterned image reflected off the intraoral dental object of interest; (c) a processing system configured to convert the patterned image into a three-dimensional model; and (d) a presentation system configured to present the three-dimensional model.

Example 2

The disclosure of the previous or any of the subsequent Examples, wherein the graph is one of a Fibonacci cube graph and a hypercube graph.

Example 3

The disclosure of any of the previous or any of the subsequent Examples, wherein the acquisition system comprises an illumination module, wherein the illumination module is configured to actuate a light modulator in accordance with the at least one selected pattern to project the at least one selected pattern onto the intraoral dental object of interest.

Example 4

The disclosure of any of the previous or any of the subsequent Examples, wherein the light modulator is one of a digital light processing (DLP) element and a digital micromirror device (DMD).

Example 5

The disclosure of any of the previous or any of the subsequent Examples, wherein the light modulator comprises a plurality of mirrors.

Example 6

The disclosure of any of the previous or any of the subsequent Examples, wherein the acquisition system comprises an imaging module, wherein the illumination module projects the at least one selected pattern through the imaging module to the intraoral dental object of interest.

Example 7

The disclosure of any of the previous or any of the subsequent Examples, wherein the imaging module comprises: (a) a varifocal lens having a dynamically adjustable index of refraction, wherein the at least one selected pattern passes through the varifocal lens; and (b) an actuation element, wherein the actuation element is configured to dynamically adjust the index of refraction.

Example 8

The disclosure of any of the previous or any of the subsequent Examples, wherein the varifocal lens comprises: (a) a membrane defining a fluid pocket, wherein the membrane comprises a shape-changing polymer; and (b) an amount of fluid disposed in the fluid pocket.

Example 9

The disclosure of any of the previous or any of the subsequent Examples, wherein the actuation element adjusts the index of refraction by varying an electric current gradient.

Example 10

The disclosure of any of the previous or any of the subsequent Examples, wherein the actuation element adjusts the index of refraction by varying an acoustic gradient.

Example 11

The disclosure of any of the previous or any of the subsequent Examples, wherein the acquisition system comprises a sensor module, wherein the sensor module is configured to: (a) receive the patterned image; (b) determine if the patterned image is out of focus; and (c) upon determining that the patterned image is out of focus, signal a correction offset to the imaging module, wherein the actuation element dynamically adjusts the index of refraction based at least in part on the correction offset.

Example 12

A method of scanning an intraoral dental object of interest comprising: (a) creating a pattern based on a Hamiltonian path traversal of a graph; (b) illuminating an intraoral dental object of interest with the pattern; (c) recording a patterned image reflected off the intraoral dental object of interest; (d) converting the patterned image into a three-dimensional model; and (e) presenting the three-dimensional model on a visual display.

Example 13

The disclosure of any of the previous or any of the subsequent Examples, further comprising actuating a light modulator in accordance with the pattern to project the pattern onto the intraoral dental object of interest.

Example 14

The disclosure of any of the previous or any of the subsequent Examples, wherein the light modulator comprises a plurality of mirrors and is one of a digital light processing (DLP) element and a digital micromirror device (DMD).

Example 15

The disclosure of any of the previous or any of the subsequent Examples, further comprising projecting the pattern through a varifocal lens prior to the intraoral dental object of interest, wherein the varifocal lens includes a dynamically adjustable index of refraction.

Example 16

The disclosure of any of the previous or any of the subsequent Examples, further comprising actuating a membrane of the varifocal lens to dynamically adjust the index of refraction, wherein the membrane is comprised of a shape-changing polymer.

Example 17

The disclosure of any of the previous or any of the subsequent Examples, further comprising varying one of an electric gradient and an acoustic gradient to adjust the index of refraction.

Example 18

The disclosure of any of the previous or any of the subsequent Examples, further comprising:
(a) determining if the patterned image is out of focus;
(b) upon determining that the patterned image is out of focus, determining a correction offset; and
(c) adjusting the index of refraction based at least in part on the correction offset.

Example 19

The disclosure of any of the previous or subsequent Examples, wherein the graph is a Fibonacci cube graph.

Example 20

The disclosure of any of the previous Examples, wherein the graph is a hypercube graph.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An intraoral dental scanning system comprising:
    (a) a plurality of patterns, wherein each pattern is based at least in part on a Hamiltonian path traversal of a graph;
    (b) an acquisition system configured to illuminate an intraoral dental object of interest with at least one selected pattern from the plurality of patterns and record a patterned image reflected off the intraoral dental object of interest;
    (c) a processing system configured to convert the patterned image into a three-dimensional model; and
    (d) a presentation system configured to present the three-dimensional model.

2. The scanning system of claim 1, wherein the graph is one of a Fibonacci cube graph and a hypercube graph.

3. The scanning system of claim 2, wherein the acquisition system comprises an illumination module, wherein the illumination module is configured to actuate a light modulator in accordance with the at least one selected pattern to project the at least one selected pattern onto the intraoral dental object of interest.

4. The scanning system of claim 3, wherein the light modulator is one of a digital light processing (DLP) element and a digital micromirror device (DMD).

5. The scanning system of claim 3, wherein the light modulator comprises a plurality of mirrors.

6. The scanning system of claim 3, wherein the acquisition system comprises an imaging module, wherein the illumination module projects the at least one selected pattern through the imaging module to the intraoral dental object of interest.

7. The scanning system of claim 6, wherein the imaging module comprises:
    (a) a varifocal lens having a dynamically adjustable index of refraction, wherein the at least one selected pattern passes through the varifocal lens; and
    (b) an actuation element, wherein the actuation element is configured to dynamically adjust the index of refraction.

8. The scanning system of claim 7, wherein the varifocal lens comprises:
    (a) a membrane defining a fluid pocket, wherein the membrane comprises a shape-changing polymer; and
    (b) an amount of fluid disposed in the fluid pocket.

9. The scanning system of claim 8, wherein the actuation element adjusts the index of refraction by varying an electric current gradient.

10. The scanning system of claim 8, wherein the actuation element adjusts the index of refraction by varying an acoustic gradient.

11. The scanning system of claim 8, wherein the acquisition system comprises a sensor module, wherein the sensor module is configured to:
    (a) receive the patterned image;
    (b) determine if the patterned image is out of focus; and
    (c) upon determining that the patterned image is out of focus, signal a correction offset to the imaging module, wherein the actuation element dynamically adjusts the index of refraction based at least in part on the correction offset.

12. A method of scanning an intraoral dental object of interest comprising:
    (a) creating a pattern based on a Hamiltonian path traversal of a graph;
    (b) illuminating an intraoral dental object of interest with the pattern;
    (c) recording a patterned image reflected off the intraoral dental object of interest;
    (d) converting the patterned image into a three-dimensional model; and
    (e) presenting the three-dimensional model on a visual display.

13. The method of claim 12, further comprising actuating a light modulator in accordance with the pattern to project the pattern onto the intraoral dental object of interest.

14. The method of claim 13, wherein the light modulator comprises a plurality of mirrors and is one of a digital light processing (DLP) element and a digital micromirror device (DMD).

15. The method of claim 14, further comprising projecting the pattern through a varifocal lens prior to the intraoral dental object of interest, wherein the varifocal lens includes a dynamically adjustable index of refraction.

16. The method of claim 15, further comprising actuating a membrane of the varifocal lens to dynamically adjust the index of refraction, wherein the membrane is comprised of a shape-changing polymer.

17. The method of claim 16, further comprising varying one of an electric gradient and an acoustic gradient to adjust the index of refraction.

18. The method of claim 17, further comprising:
(a) determining if the patterned image is out of focus;
(b) upon determining that the patterned image is out of focus, determining a correction offset; and
(c) adjusting the index of refraction based at least in part on the correction offset.

19. The method of claim 18, wherein the graph is a Fibonacci cube graph.

20. The method of claim 18, wherein the graph is a hypercube graph.

* * * * *